US00PP28232P3

(12) United States Plant Patent
Skotak, Jr.

(10) Patent No.: US PP28,232 P3
(45) Date of Patent: Aug. 1, 2017

(54) ***ANANAS* PLANT NAMED DURANAS3**

(50) Latin Name: ***Ananas comosus* (L.) Merr.**
Varietal Denomination: Duranas3

(71) Applicant: Chester Skotak, Jr., Alajuela (CR)

(72) Inventor: Chester Skotak, Jr., Alajuela (CR)

( * ) Notice: Subject to any disclaimer, the term of this patent is extended or adjusted under 35 U.S.C. 154(b) by 97 days.

(21) Appl. No.: 14/757,212

(22) Filed: Dec. 4, 2015

(65) Prior Publication Data

US 2016/0278255 P1 Sep. 22, 2016

(30) Foreign Application Priority Data

Mar. 17, 2015 (QZ) ..... PBR 2015/0609

(51) Int. Cl.
*A01H 5/08* (2006.01)

(52) U.S. Cl.
USPC ..... Plt./156

(58) Field of Classification Search
USPC ..... Plt./156
See application file for complete search history.

*Primary Examiner* — Anne Grunberg
(74) *Attorney, Agent, or Firm* — Samuel R. McCoy, Jr.

(57) ABSTRACT

A new and distinct *Ananas* cultivar named 'Duranas3' which is characterized by the combination of a compact plant size, greyed-purple to brown foliage, strongly reflexed foliage, dark red fruit, and the stability of all characteristics from generation to generation.

4 Drawing Sheets

Latin name of genus and species: The Latin name of the genus and species of the novel variety disclosed herein is *Ananas comosus* (L.) Merr.

Variety denomination: The inventive variety of *Ananas* disclosed herein has been given the variety denomination 'Duranas3'.

CROSS REFERENCE TO RELATED APPLICATIONS

This application claims priority to the Community Plant Variety Rights application number 2015/0609, filed Mar. 17, 2015, which is herein incorporated by reference.

BACKGROUND OF THE INVENTION

The present invention relates to a new and distinct *Ananas comosus*, ornamental pineapple. *Ananas comosus* is often planted for its tropical appearance and for its horticultural novelty. Its market class is PLT/156.

Parentage: The *Ananas comosus* variety 'Duranas3' is the result of a controlled pollination breeding program carried out in March of 2007 at a commercial greenhouse in Palmares, Costa Rica. 'Duranas3' is a progeny of said breeding program which resulted from the cross pollination of a *Ananas comosus* female breeding line, identified by the breeding code "03#12", and a *Ananas comosus* male breeding line, identified by the breeding code "16#1". Both of breeding lines were developed and owned by the inventor and were never commercially released. Progeny of said cross were observed for desired commercial characteristics and, in June of 2009, 'Duranas3' was selected for its compact inflorescence and dark red fruit.

Asexual Reproduction: 'Duranas3' was first asexually propagated by mericloning in June 2009 at a laboratory in Sleidinge, Belgium and has since been asexually propagated through eight additional generation. Through subsequent generations, the unique features of this cultivar are stable and reproduced true to type.

SUMMARY OF THE INVENTION

The following characteristics have been repeatedly observed and represent the distinguishing characteristics of the new *Ananas* cultivar, 'Duranas3'. These traits, in combination, distinguish 'Duranas3' as a new and distinct cultivar:

1. 'Duranas3' exhibits a small, compact plant size; and
2. 'Duranas3' exhibits greyed-purple to brown foliage; and
3. 'Duranas3' exhibits strongly reflexed foliage; and
4. 'Duranas3' exhibits dark red fruit.

DETAILED BOTANICAL DESCRIPTION

Figure 1:
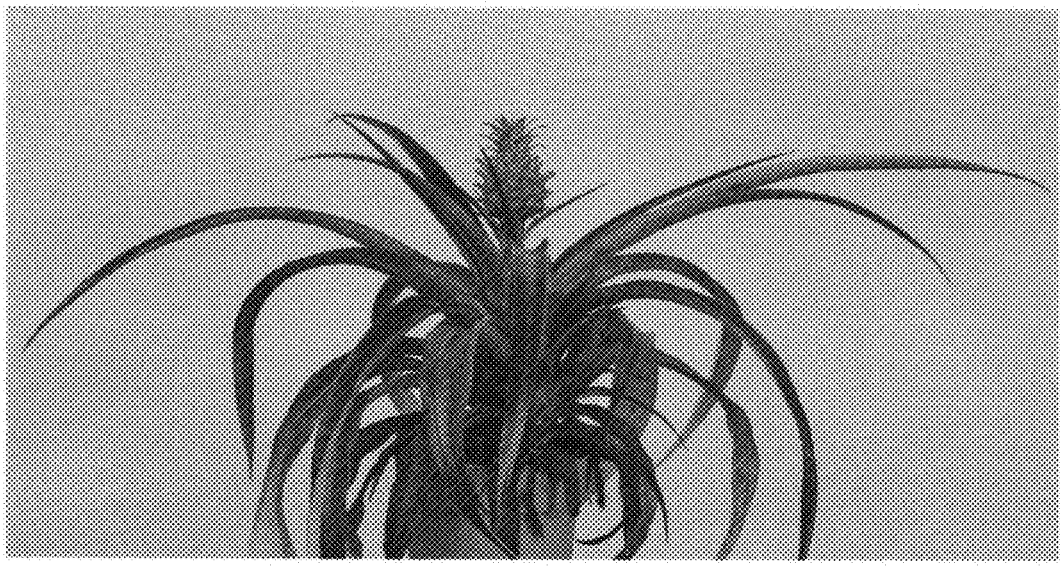
FIG. 1 illustrates, as nearly true as it is reasonably possible to make the same in color photographs of this type, an exemplary plant of 'Duranas3' grown at a commercial greenhouse in Bergschenhoek, The Netherlands. This plant is approximately 20 months old, shown planted in a 12 cm container.
Figure 2:
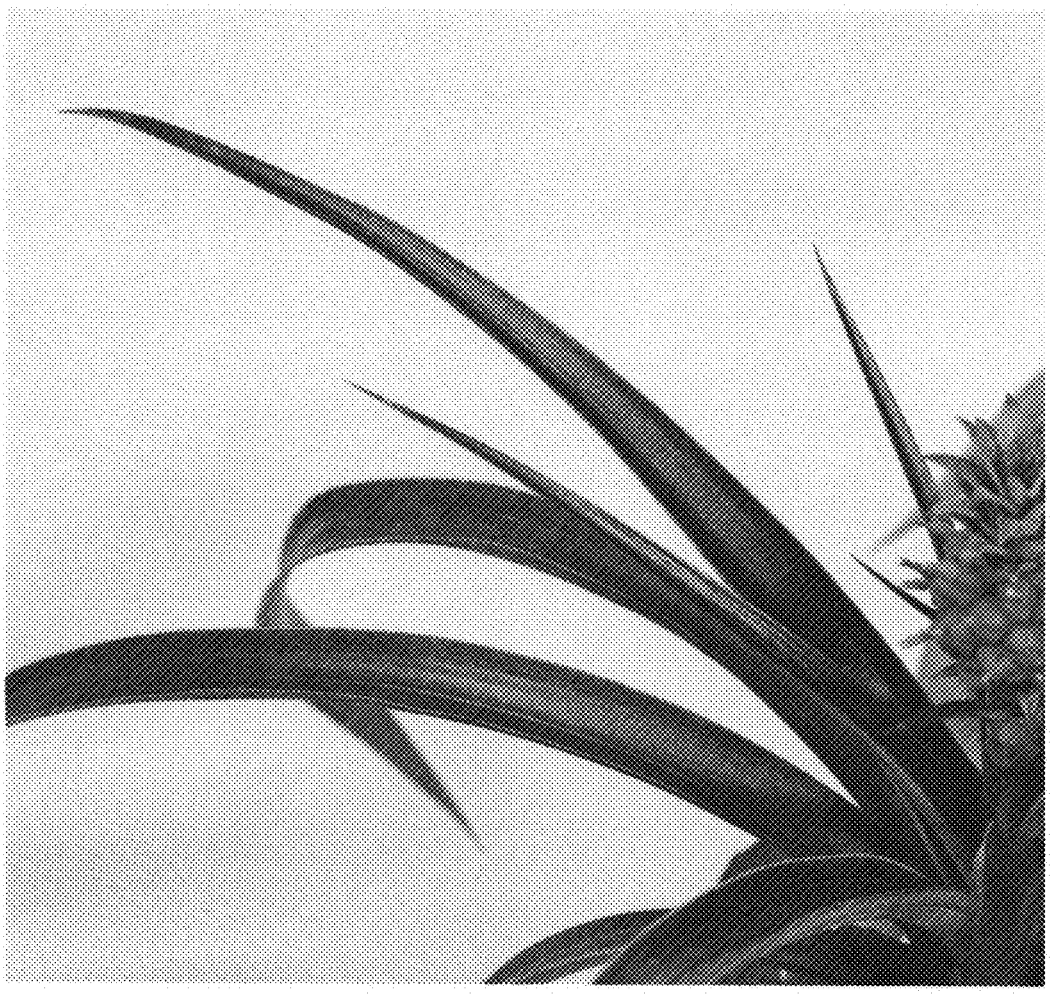
FIG. 2 illustrates, as nearly true as it is reasonably possible to make the same in color photographs of this type, the typical foliage of 'Duranas3'.
Figure 3:
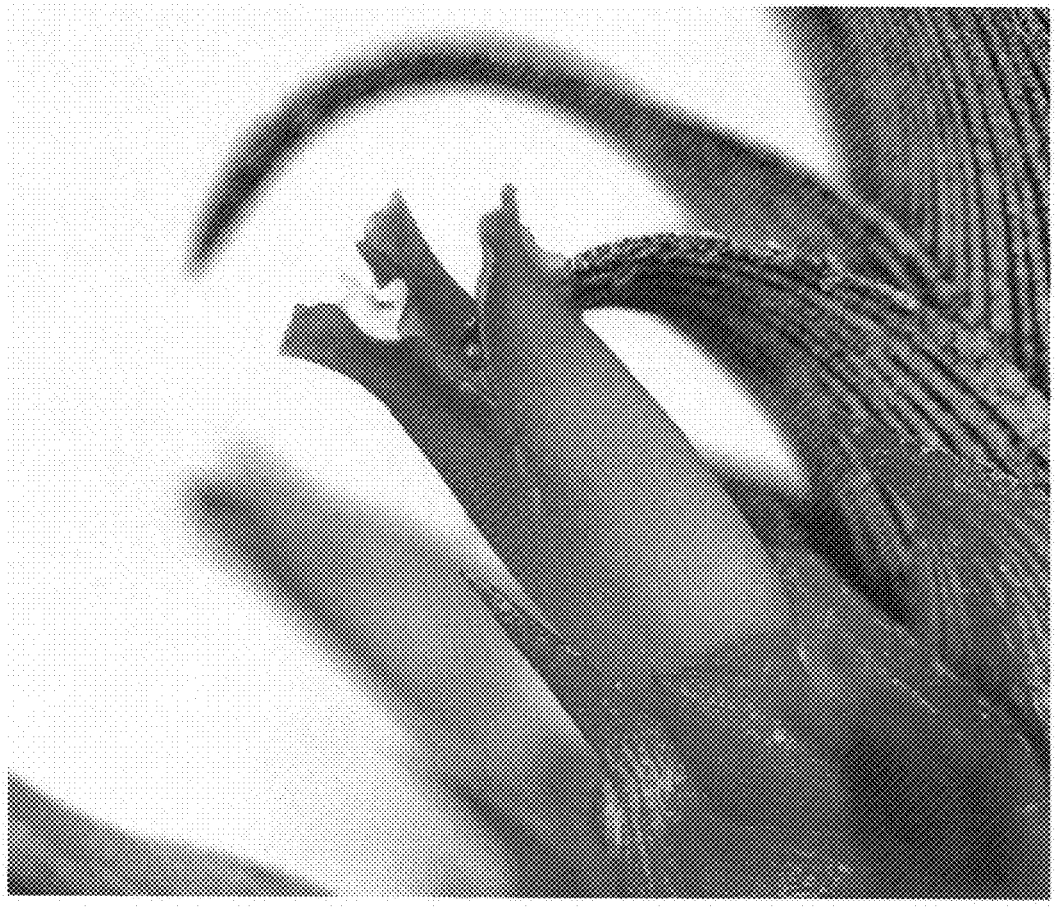
FIG. 3 illustrates, as nearly true as it is reasonably possible to make the same in color photographs of this type, the typical flower of 'Duranas3'.
Figure 4:
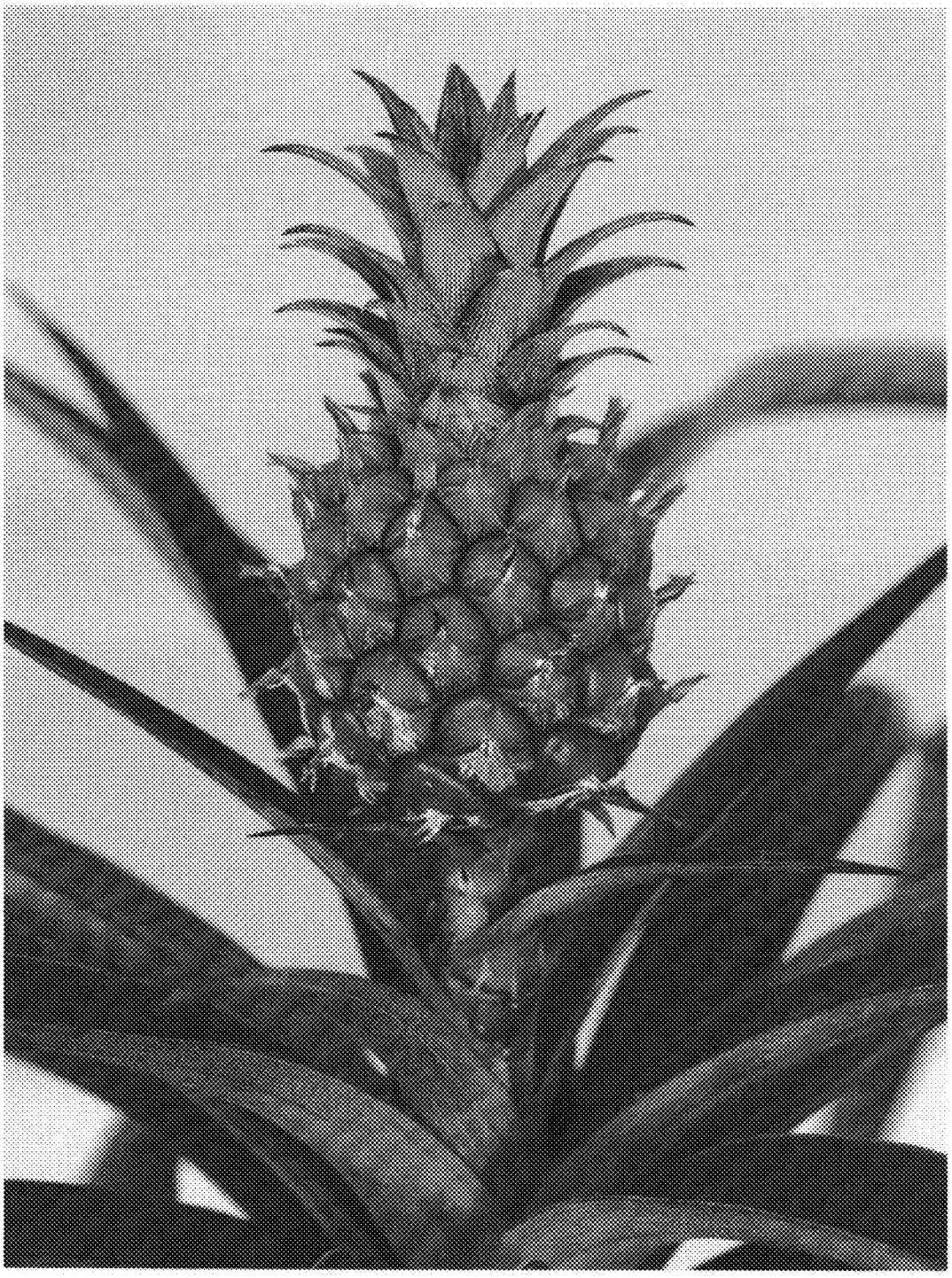
FIG. 4 illustrates, as nearly true as it is reasonably possible to make the same in color photographs of this type, the typical fruit of 'Duranas3'.

The following observations and measurements made in September of 2015 describe averages from a sample set of six specimens of 20 month-old 'Duranas3' plants grown in 12 cm nursery pots at a commercial greenhouse in Bergschenhoek, The Netherlands. Plants were grown under light maximum light levels of approximately 10,000 lux. Plants were maintained with a weekly fertigation program and regularly watered with overhead irrigation. No chemical pest measures were taken.

Those skilled in the art will appreciate that certain characteristics will vary with older or, conversely, with younger plants. 'Duranas3' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2015 (sixth edition).

A botanical description of 'Duranas3' and comparisons with other varieties of *Ananas comosus* are provided below.

General plant description:

*Growth habit*.—Perennial; monopodial. Leaves arranged in a basal rosette and the inflorescence grows from the center of the basal rosette.

*Average height*.—Average of 21.0 cm.

*Plant spread*.—Average of 59.0 cm.

*Growth rate*.—Low to moderate.

*Propagation type*.—Mericloning.

*Disease resistance or tolerance*.—Similar to other *Ananas comosus* varieties.

*Pest resistance or tolerance*.—Similar to other *Ananas comosus* varieties.

*Temperature tolerances*.—USDA Zones 10 to 12; at least tolerant of temperatures to 40 degrees Celsius.

Root system: Typical of the species.

Foliage:

*Arrangement*.—Rosette; one mature basal rosette and one immature basal rosette. No stems or lateral branches, the leaves form a stem-like structure not consisting of a stem as such, but only consisting of the leaf sheaths.

*Quantity of leaves*.—Approximately 31 leaves per rosette.

*Durability of foliage to stress*.—Very high.

*Lamina*.—Dimensions — 38.1 cm long, excluding the sheath, and 2.2 cm wide. Thickness — Approximately 0.9 cm. Shape of blade — Ligulate. Aspect — Leaves held at an angle of approximately 45 degrees from horizontal and strongly reflexed (with the leaf apex pointing at an approximate angle of minus−90 degrees from horizontal). Apex — Acuminate. Base — Sheathing. Margin — Entire and slightly undulated towards the apex. Pubescence, texture and luster of adaxial surface — Glabrous, smooth and moderately glossy. Pubescence, texture and luster of abaxial surface — Glabrous, smooth and matte. Color — Juvenile foliage, adaxial surface — Brown, RHS 200A, and covered with a waxy layer that is colored black, RHS 202C to 202D. Juvenile foliage, abaxial surface — Brown, RHS 200B, and covered with a waxy layer that is colored greyed-purple to black, in between RHS N187D and 202D. Mature foliage, adaxial surface — Greyed-purple to brown, in between N186C and 200A yet closest to 200A, and margined yellow-green, approximating to darker-than RHS 147A; the surface is covered with a waxy layer that is colored greyed-purple to black, in between RHS N187D and 202D. Mature foliage, abaxial surface — Yellow-green, RHS 152A, and covered with a waxy layer that is colored greyed-purple to black, in between RHS N187D and 202D. Venation — Parallel. Mature foliage venation, adaxial surface — Same color as foliage; greyed-purple to brown, in between N186C and 200A yet closest to 200A, and margined yellow-green, approximating to darker-than RHS 147A. Mature foliage venation, abaxial surface — Same color as foliage; yellow-green, RHS 152A. Sheath — Sheath length — Average 3.4 cm. Sheath width — Average 3.4 cm. Sheath color, adaxial and abaxial surfaces — Yellow-green, RHS N148D, and margined with greyed-orange, RHS 166C.

Inflorescence:

*Inflorescence arrangement*.—Spike inflorescence arising from the center of the foliage rosette; lowest flowers opening first.

*Flowering habit*.—Once a year, continuously.

*Natural flowering season*.—Summer into late summer.

*Time to flower*.—Approximately 10 months.

*Inflorescence quantity*.—One.

*Flowers per inflorescence*.—Average of 38.

*Inflorescence height*.—Average of 7.8 cm, excluding the peduncle.

*Inflorescence diameter*.—Average of 5.4 cm.

*Peduncle*.—Dimensions — Approximately 12.9 cm long, to the base of the inflorescence, and 1.2 cm wide. Aspect — Approximately 90-degree angle to horizontal. Strength — Very strong. Color — Yellow-green to brown, in between 147A and 200A yet closest to 200A, and covered with a waxy layer that is colored greyed-purple to black, in between RHS N187D and 202D.

*Pedunculate leaves*.—Quantity — Average of 4. Dimensions — Average length is 8.2 cm and the average width is 0.7 cm. Apex — Long acuminate. Base — Sheathing Margins — Entire. Color, adaxial surface — Greyed-purple to brown, in between N186C and 200A yet closest to 200A, and margined yellow-green, approximating to darker-than RHS 147A; the surface is covered with a waxy layer that is colored greyed-purple to black, in between RHS N187D and 202D. Color, abaxial surface — Yellow-green, RHS 152A, and covered with a waxy layer that is colored greyed-purple to black, in between RHS N187D and 202D. Sheath color, both surfaces — Red, RHS N45D.

*Crown*.—General — Inflorescence is terminated with a cluster of small leaves, typical of the species. Quantity of leaves — 32. Leaves of the crown — Shape — Narrow deltoid. Dimensions — Average length is 3.5 cm; average width is 0.8 cm. Apex — Acuminate. Base — Sheathing. Margins — Entire. Color, both surfaces — Brown, RHS 200D, and covered with a waxy layer that is colored greyed-purple to black, in between RHS N187D and 202D. Sheath — Dimensions — Average length is 1.0 cm, and the average width is 1.5 cm. Color, both surfaces — Yellow-green, RHS 145A.

Bud:

*Length*.—Average of 0.6 cm.

*Diameter*.—Average of 0.25 cm.

*Shape*.—Narrow triangular.

*Texture and luster*.—Glabrous and slightly glossy.

*Color*.—Violet. RHS 83D.

Flower:

*Flower type and form*.—Single; tubular.

*Attachment*.—Sessile.

*Aspect*.—Upright.

*Diameter*.—Average of 0.5 cm.

*Depth*.—Approximately 1.4 cm.

*Fragrance*.—No fragrance.

*Lastingness*.—2 days.

*Persistent*.—Persistent.

*Petals*.—Quantity of Petals — 3. Arrangement — Rotate; single whorl of unfused petals. Length — Approximately 1.4 cm. Width — Approximately 0.35 cm. Shape — Oblanceolate. Apex — Acute. Margin — Entire. Pubescence, texture and luster — Glabrous, moderately velvety, and matte. Color when opening, upper surface — Violet, RHS N88B to N88C, and becoming white, RHS 155C, towards the base. Color when opening, lower surface — Violet, RHS N88C, and becoming white, RHS 155C, towards the base. Color when fully opened, upper surface — Violet, RHS N88C, and becoming white, RHS 155C, towards the base. Color when fully opened, lower surface — Violet, RHS N88C, and becoming white, RHS 155C, towards the base. Fading, upper surface — Not fading. Fading, lower surface — Not fading. Venation color, fully opened, upper surface — Greyed-orange, RHS 165B. Venation color, fully opened, lower surface — Greyed-orange, RHS 165B.

*Calyx*.—Shape — Rotate. Length — Average of 0.6 cm. Diameter — Average of 0.8 cm.

*Sepals*.—Quantity — Three. Arrangement — Rotate. Length — Average of 0.6 cm. Width — Average of 0.5 cm. Shape — Deltoid. Apex — Acute. Base — Cuneate. Margin — Entire. Pubescence, texture and luster — Glabrous and glossy. Immature color, upper surface — Red, RHS 53B. Immature color, lower surface — Red, RHS 53B; base is yellow-green, RHS 144C to 144D. Mature color, upper surface — Red, RHS 53B. Mature color, lower surface — Red, RHS 53B; base is yellow-green, RHS 144C to 144D.

Reproductive organs:

*Stamens*.—Quantity — Six, on average. Anthers — Shape — Basifixed; narrow sagittate. Length — 0.2 cm, on average. Color — Greyed-yellow, RHS 160D. Filaments — Length — 1.0 cm, on average. Color — White, RHS NN155C. Pollen — Abundance — Low. Color — Yellow, RHS 11D.

*Pistil*.—Quantity — One, on average. Length — 1.3 cm. Style — Length — 1.2 cm. Color — White, RHS NN155C. Stigma — Shape — Three-lobed. Color — White, RHS NN155C. Ovary Color — Yellow-green, RHS 150D.

Fruit and seed:

*Fruit*.—General — A syncarp which is comprised of multiple of berries, coalescing as they mature, to form the fleshy "pineapple". Quantity of berries — Approximately 38 per inflorescence. Shape of berries — Hexagonal; typical for *Ananas comosus*. Dimension of berries — Average length is 0.5 cm; average width is 1.2 cm. Pubescence and luster — Glabrous and glossy. Color of berries — Greyed-purple, RHS 187A to 187B. Time to ripening of fruit — Two weeks, on average. Fruit taste — Tasteless; not suitable for consumption.

*Seed*.—Not present.

COMPARISONS WITH THE PARENTS

The breeding line parents of 'Duranas3' were never commercialized and are no longer in cultivation. Therefore, a comparison of 'Duranas3' with its parents is unavailable.

COMPARISON WITH THE MOST SIMILAR *ANANAS* CULTIVAR KNOWN TO THE INVENTOR

'Duranas3' is similar in many horticultural characteristics to the commercial cultivar *Ananas* 'Duranas2' (Community Plant Variety Rights application number 2012/2017). However 'Duranas3' differs from 'Duranas2' in the following characteristics:

1. The fruit of 'Duranas3' exhibits a dark red general tonality, whereas the fruit of 'Duranas2' exhibits a yellow general tonality.
2. 'Duranas3' exhibits a small and compact plant size, whereas 'Duranas2' exhibits a larger and less compact plant size.

That which is claimed:

1. A new and distinct variety of *Ananas* plant named 'Duranas3', as described and illustrated herein.

* * * * *